United States Patent
Sakamoto et al.

(10) Patent No.: US 10,765,386 B2
(45) Date of Patent: Sep. 8, 2020

(54) RADIOGRAPHIC APPARATUS

(71) Applicant: SHIMADZU CORPORATION, Kyoto (JP)

(72) Inventors: Yuki Sakamoto, Kyoto (JP); Takeshi Okamoto, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 205 days.

(21) Appl. No.: 16/115,679

(22) Filed: Aug. 29, 2018

(65) Prior Publication Data

US 2020/0069270 A1 Mar. 5, 2020

(51) Int. Cl.
*A61B 6/00* (2006.01)

(52) U.S. Cl.
CPC .......... *A61B 6/4441* (2013.01); *A61B 6/4233* (2013.01); *A61B 6/4405* (2013.01); *A61B 6/4452* (2013.01)

(58) Field of Classification Search
CPC . A61B 36/4452; A61B 6/4441; A61B 6/4233; A61B 6/4405
See application file for complete search history.

(56) References Cited

U.S. PATENT DOCUMENTS 6,222,906 B1* 4/2001 Sakaguchi .............. A61B 6/06
257/E27.132

FOREIGN PATENT DOCUMENTS

| JP | 11-318877 | 11/1999 |
| JP | 2013-158532 | 8/2013 |
| WO | WO 2012/042033 | 4/2012 |

OTHER PUBLICATIONS

JP 2016-042080, Notification of Reasons for Refusal, dated Feb. 27, 2019, 3 pages—English, 4 pages—Japanese.

* cited by examiner

*Primary Examiner* — David P Porta
*Assistant Examiner* — Fani Boosalis
(74) *Attorney, Agent, or Firm* — Andrew F. Young, Esq.; Lackenbach Siegel, LLP

(57) ABSTRACT

A radiation imaging apparatus avoids collisions of the radiation with an obstacle, and includes a flat panel detector (FPD) connected with a supporting axis facing a vertical direction to a ray detection surface. A supporting axis is supported rotatably due to the action of the bearing and the flat panel detector rotates around the supporting axis as the center of the rotation via the supporting axis by driving with the motor. A frame member surrounding the flat panel detector has a circular outer appearance of which a center is the supporting axis, and the diameter of the frame member is longer than the length of the diagonal line of the flat panel detector.

3 Claims, 7 Drawing Sheets

RADIOGRAPHIC APPARATUS

CROSS REFERENCE TO RELATED APPLICATIONS

This application relates to, but does not claim priority from, JP 2016-042080 filed Mar. 4, 2016 and published as JP 2017-153861 on Sep. 7, 2017, the entire contents of which are incorporated herein by reference.

FIGURE SELECTED FOR PUBLICATION

FIG. 4.

BACKGROUND OF THE INVENTION

Field of the Invention

The present invention relates to a radiation imaging apparatus comprising a rotatable radiation detector.

Description of the Related Art

FIG. 6 is a perspective view illustrating a conventional X-ray imaging apparatus as such a radiation imaging apparatus.

Such an X-ray imaging apparatus comprises an examination table 1 and a X-ray imaging unit 2 that performs an X-ray imaging or an X-ray fluoroscopy on the subject on the examination table 1.

The examination table 1 comprises a table 11, on which the subject is loaded, a frame 12 and a pedestal 13. The table 11 is supported to be movable in the longitudinal direction of the table 11 relative to the frame 12. In addition, as set forth above, the frame 12 is supported to be movable in the short direction of the table 11 relative to Pedestal 13.

The X-ray imaging unit 2 further comprises an X-ray irradiation unit 31 comprising an X-ray tube and a collimator and a flat panel detector 32 that detects the X-ray which is irradiated from the X-ray irradiation unit 31 and transmits through the subject on the examination table 1. In addition, the X-ray imaging unit 2 further comprises a C-arm 28, having approximately a letter C shape, that comprises a circular guide and supports the X-ray irradiation element 31 and the flat panel detector 32 while facing each other, a slide mechanism 27 that supports the C-arm 28 to be slidable by connecting with the guide of the C-arm 28, a rotation mechanism 29 that supports the slide mechanism 27 to be rotatable, and a support element 26 that supports the rotation mechanism 29.

The support element 26 is supported through the rotation member 25 that rotates around the vertical axis relative to the movement member 24. In addition, the movement member 24 is movable along rails, not shown in FIG., in the X-direction and Y-direction orthogonal to each other. Therefore, the C-arm 28 is movable along with the X-ray irradiation element 31 and the flat panel detector 32 in the X-direction and Y-direction, rotatable around the vertical axis, rotatable around the horizontal direction, and slidable relative to the slide mechanism 27.

The flat panel detector 32 is rotatable around the axis facing the vertical direction to the X-ray detection surface relative to the C-arm 28. Further, the outer appearance (visual shape from the X-ray detection surface) of the flat panel detector 32 looks rectangular (refer to Patent Document 1).

RELATED PRIOR ART DOCUMENT

Patent Document 1: JP Patent Published 2013-158532 A1

ASPECTS AND SUMMARY OF THE INVENTION

Objects to Be Solved

FIG. 7 is a schematic view illustrating the aspect of the flat panel detector 32 that rotates around the axis facing the vertical direction to the X-ray detection surface.

Referring to FIG. 7, the outer appearance of the flat panel detector 32 looks rectangular. Therefore, when the flat panel detector 32 rotates around the axis facing the vertical direction to the X-ray detection surface, given the obstacle 51 is in-place in the proximity of the flat panel detector 32, it is problematic that the flat panel detector 32 and the obstacle 51 collide with each other. Accordingly, when the flat panel detector 32 rotates, the likelihood of collision of the flat panel detector 32 with the obstacle 51 must be always examined, so that it is problematic that the operation thereof is bothersome.

The purpose of the present invention is to solve the above objects and to provide a radiation imaging apparatus that facilitates to avoid the collision with the obstacle when the radiation detector rotates.

Means for Solving The Problem

According to the aspect of the invention claimed in claims, a radiation imaging apparatus comprises: a radiation detector, an arm supporting the radiation detector, and a rotation mechanism that rotates the radiation detector around the axis facing the vertical direction to the radiation detection surface relative to the arm; wherein a frame member has a circular form, of which center is the above axis, that is the outer shape surrounding the radiation detector and is installed to the circumference of the radiation detection surface of the radiation detector.

As the one aspect of the invention claimed in the claims, the outer frame member is a wheel forming the outer shape that is a circle.

According to another aspect of the invention claimed in claims, the radiation detector is a flat panel detector.

According to another aspect of the invention claimed in claims, the frame member has an outer shape of which diameter is longer than the diagonal length of the flat panel detector.

Effect of the Invention

According to the aspect of the invention claimed in claims, even when rotating the radiation detector, the collision of the radiation detector with the obstacle is prevented from an occurrence due to the action of the frame member installed in the circumference of the radiation detector.

According to another aspect of the invention claimed in claims, movement or rotation of the radiation detector is carried out using the wheel and the collision of the radiation detector with the obstacle is prevented due to the action of the wheel.

According to another aspect of the invention claimed in claims, a collision of the rectangular flat panel detector with the obstacle is avoidable.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
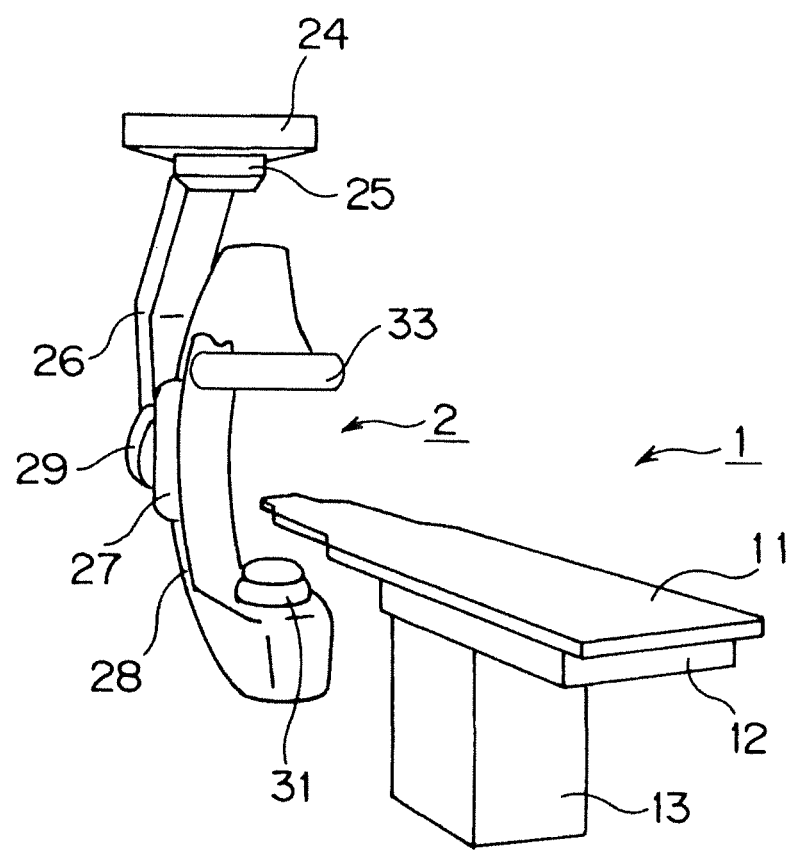
FIG. 1 is a perspective view illustrating an X-ray imaging apparatus according to the aspect of the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' or 'connect' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Figure 2:
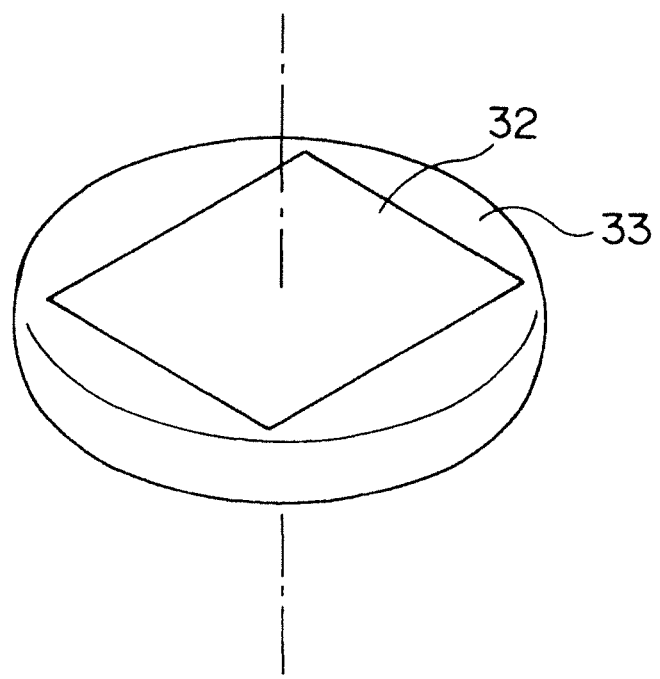
FIG. 2 is a perspective view illustrating the flat panel detector 32 together with the frame member 33.
Figure 3:
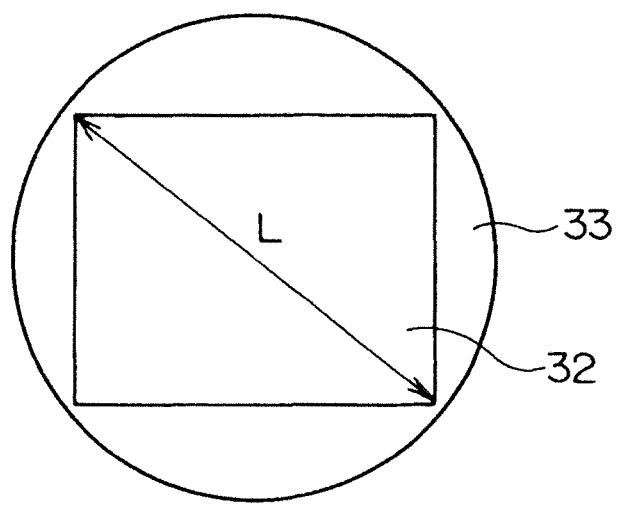
FIG. 3 is a plan view illustrating the flat panel detector 32 together with the frame member 33.

The inventors set forth Embodiments of the present invention based on the following FIGs. FIG. 1 is the perspective view illustrating an X-ray imaging apparatus as the radiation imaging apparatus according to the aspect of the present invention. FIG. 2 is the perspective view illustrating the flat panel detector 32 together with the frame member 33. FIG. 3 is the plan view illustrating the flat panel detector 32 together with the frame member 33.

Such an X-ray imaging apparatus comprises an examination table 1 on which a subject is loaded, and the X-ray imaging unit 2 that performs an X-ray imaging or an X-ray fluoroscopy on the subject on the examination table 1.

The examination table 1 comprises the table 11 on which the subject is loaded, a frame 12 and a pedestal 13. The table 11 is supported to be movable in the longitudinal direction of the table 11 relative to the frame 12. And, the frame 12 is supported to be movable in the width (short) direction of the table 11 relative to the pedestal 13.

The X-ray imaging unit 2 further comprises a radiation irradiation unit 31 comprising the X-ray tube and the collimator of the present invention, the flat panel detector 32 as an X-ray detector that detects the X-ray which is irradiated from the X-ray tube and transmits through the irradiated subject on the examination table 1, the frame member 33 of which the outer appearance surrounding the flat panel detector 32 is a circle. In addition, the X-ray imaging element 2 further comprises a C-arm 28, having approximately a letter C shape, that comprises a circular guide and supports the X-ray irradiation element 31 and the flat panel detector 32 while facing each other, a slide mechanism 27 that supports the C-arm 28 to be slidable by connecting with the guide of the C-arm 28, a rotation mechanism 29 that supports the slide mechanism 27 to be rotatable, and a support element 26 that supports the rotation mechanism 29.

The support element 26 is supported through the rotation member 25 that rotates around the vertical axis relative to the movement member 24. In addition, the movement member 24 is movable along rails, not show in FIG., in the X-direction and Y-direction orthogonal to each other. Therefore, the C-arm 28 is movable along with the X-ray irradiation element 31 and the flat panel detector 32 in the X-direction and Y-direction, rotatable around the vertical axis, rotatable around the horizontal direction, and slidable relative to the slide mechanism 27.

The flat panel detector 32 applied to such an X-ray imaging apparatus is rotatable around the supporting axis 41 (referring to FIG. 4 set forth later) facing the vertical direction to the X-ray detection surface (referring to FIG. 4 set forth later) relative to the C-arm 28. Specifically, referring to FIG. 2, the flat panel detector 32 rotates around the axis denoted as the dashed-dotted line together with the frame member 33. The outer appearance (visual shape from the X-ray detection surface) of the flat panel detector 32 looks rectangular, and the outer appearance of the frame member 33 surrounding the flat panel detector 32 looks a circle of which center is the supporting axis 41. And, the diameter of the frame member 33 is longer than the length of the diagonal line of the flat panel detector 32.

Figure 4:
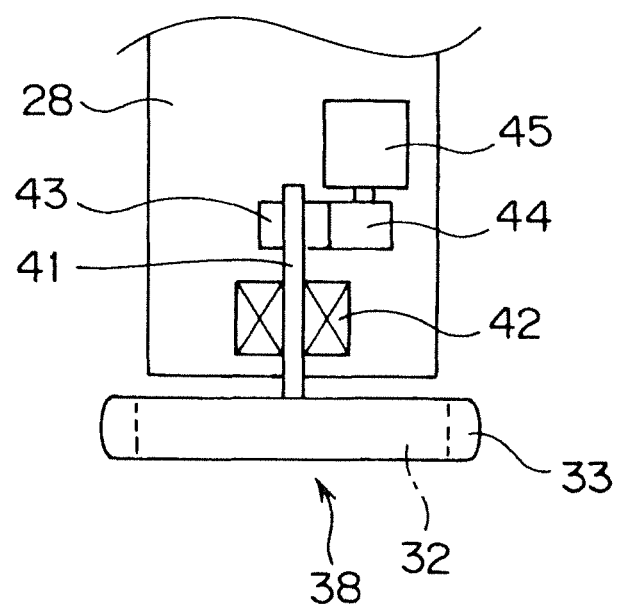
FIG. 4 is a schematic diagram illustrating the rotation mechanism that rotates the flat panel detector 32 relative to the C-arm 28.

FIG. 4 is a schematic diagram illustrating the rotation mechanism that rotates the flat panel detector 32 relative to the C-arm 28.

The flat panel detector 32 connects with the supporting axis 41 that is facing the vertical direction relative to the X-ray detection surface 38 (i.e., facing the normal direction of the X-ray detection surface 38) in the reverse side of the X-ray detection surface 38. The supporting axis 41 is in-place at the center of the flat panel detector 32 having the rectangular shape. The supporting axis 41 is supported to be rotatable with the action of the bearing 42, and the gear 43 is fixed near the upper end thereof. The gear 43 gears with the gear 44 fixed to the rotation axis of the motor 45. Therefore, the flat panel detector 32 rotates around the supporting axis 41 by driving of the motor 45.

Figure 7:
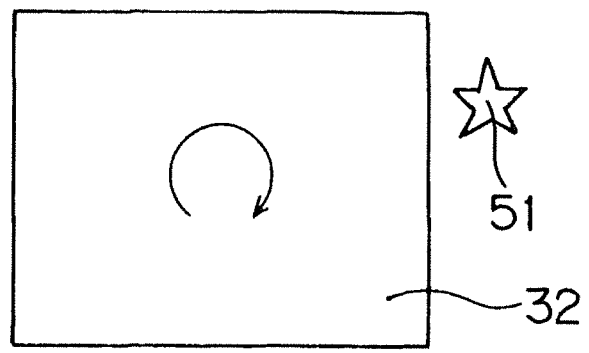
FIG. 7 is a schematic view illustrating the aspect of the flat panel detector 32 rotating around the axis facing the vertical direction to the X-ray detection surface.

With regard to the X-ray imaging apparatus having such a structure, the outer appearance of the frame member 33 installed to the circumference of the flat panel detector 32 is the circle of which center is the supporting axis 41. Accordingly, even when the flat panel detector 32 rotates around the supporting axis 41 together with the frame member 33, the location of the circumference of the frame member 33 is constant. Therefore, as illustrated referring to FIG. 7, the obstacle 51 and the flat panel detector 32 have never been in an locational relationship in which collision takes place to each other due to the action of the frame member 33. Accordingly, the collision of the flat panel detector 32 with the obstacle 51 is avoided absolutely. Therefore, the likelihood of collision of the flat panel detector 32 with the obstacle 51 is never examined when the operator rotates the flat panel detector 32, so that the operation thereof is no longer bothersome.

Figure 5:
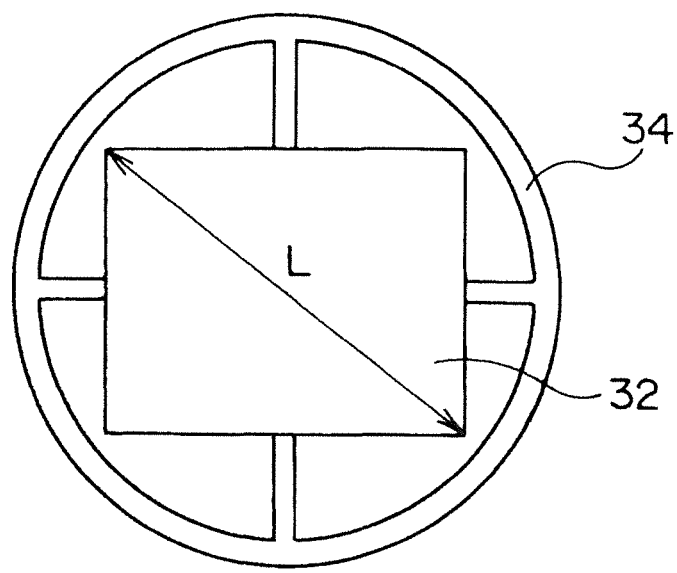
FIG. 5 is a plane view illustrating the wheel 34 that is the frame member according to the aspect of the Embodiment 2 together with the flat panel detector 32.
Figure 6:
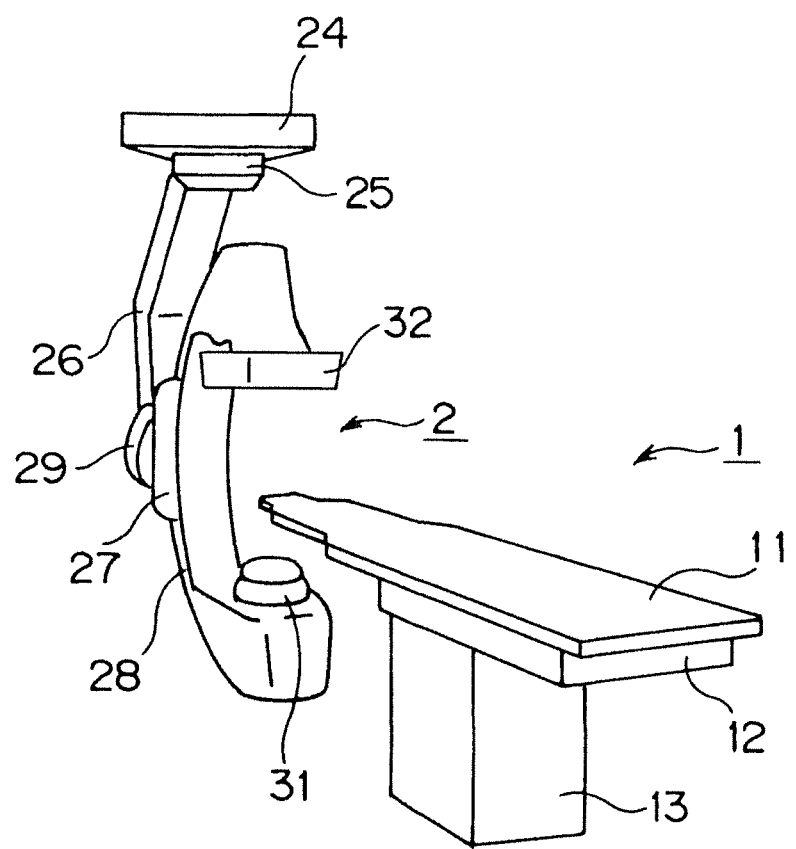
FIG. 6 is a perspective view illustrating the conventional X-ray imaging apparatus.

Next, the inventors set forth an alternative Embodiment of the present invention. FIG. 5 is a plane view illustrating the wheel 34 that is the frame member according to the aspect of the Embodiment 2 together with the flat panel detector 32.

According to the aspect of the Embodiment 2, the wheel 34 that the operator grips is adopted as the frame member. As well as the frame member 33 according to the aspect of the Embodiment 1, the wheel 34 is fixed to the flat panel detector 32 at the circumference of the flat panel detector 32. The outer appearance of such a wheel 34 is the circle of which center is the supporting axis 41. And, the diameter of the wheel 34 is longer than the length of the diagonal line of the flat panel detector 32.

With regard to the X-ray fluoroscopic imaging apparatus according to the Embodiment 2, the operator moves or rotates the flat panel detector 32 while gripping the wheel 34. And, even when the wheel 34 rotates around the supporting axis 41, the location of the circumference of the wheel 34 is constant. Therefore, the obstacle 51 and the flat panel detector 32 have never been in a locational relationship in which collision takes place to each other due to the action of the wheel 34. Accordingly, the collision of the flat panel detector 32 with the obstacle 51 is avoided absolutely. Accordingly, as well as the Embodiment 1, when the operator rotates the flat panel detector 32, the likelihood of collision of the flat panel detector 32 with the obstacle 51 is never examined, so that the operation thereof is no longer bothersome.

In addition, according to the aspect of the Embodiments set forth above, the flat panel detector 32 is supported by the supporting axis 41 and the flat panel detector 32 rotates together with the supporting axis 41, but the flat panel detector 32 supported by the other member and such a supported flat panel detector 32 can be rotated around the center that is a virtual rotation center axis facing vertical direction relative to the X-ray detection surface.

In addition, according to the aspect of the Embodiment set forth above, the inventors set forth the application of the present invention to the X-ray imaging apparatus in which the rectangular flat panel detector 32 is rotatably supported by the C-arm 28 having an approximately C-shape, but the shape of the arm supporting the flat panel detector 32 is not limited thereto, and the present invention is applicable to the radiation imaging apparatus in which a variety of radiation detectors is supported rotatably relative to the arm having the other shape.

REFERENCE OF SIGNS

1 Examination table
2 X-ray imaging unit
11 Table
28 C-arm
31 X-ray irradiation unit
32 Flat panel detector
33 Frame member
34 Wheel (handle)
38 X-ray detection surface
41 Supporting axis
42 Bearing
43 Gear
44 Gear
45 Motor It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related radiotherapy imaging devices, systems, and arrangements, including related radiotherapy tracking computers and operational controls and technologies of radiographic devices and all their sub components, including various circuits and components and combinations of circuits and combinations of components for such devices and for all related hand held type devices, without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, operating circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuit illustrations, step-modes, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

Those of skill in the particular art will be recognized as having and having access to sophisticated radiotherapy tracking systems, circuits, and methods such that the skill level is high in science, technology, computers, programming, circuit design, and arrangement such that the described elements herein, after and following a review of this inventive disclosure and the inventive details herein, will be understood by those of skill in the art.

Also, the inventors intend that only those claims which use the words "means for" (specifically requiring the phrase "for" in "means for") are intended to be interpreted under 35 USC 112. Moreover, no limitations from the specification are intended to be read into any claims, unless those limitations are expressly included in the claims.

It will be further understood that the method steps described herein shall be understood additionally as descriptive algorithms for the operation of the enclosed units, switches, modes, and devices and units to which they apply.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A radiation imaging apparatus, comprising:
   a radiation detector;
   an arm that supports said radiation detector;
   a rotation mechanism that rotates said radiation detector around an axis facing a vertical direction to a radiation detection surface relative to said arm;
   wherein a frame member that has a circular form, which has a center aligned with said axis, and further includes an outer shape surrounding said radiation detector and is installed relative to a circumference of a radiation detection surface of said radiation detector; and
   wherein said frame member is a handle forming an outer appearance that is a circle.

2. The radiation imaging apparatus, according to claim 1, wherein:
   said radiation detector is a flat panel detector.

3. The radiation imaging apparatus according to claim 2, wherein:
   said frame member has a diameter that is longer than a diagonal length of said flat panel detector.

\* \* \* \* \*